United States Patent [19]

Kee

[11] Patent Number: 5,377,672
[45] Date of Patent: Jan. 3, 1995

[54] SUCTION CONTROL VALVE

[75] Inventor: Kok-Hiong Kee, St. Louis, Mo.

[73] Assignee: Sherwood Medical Company, St. Louis, Mo.

[21] Appl. No.: 168,738

[22] Filed: Dec. 15, 1993

Related U.S. Application Data

[62] Division of Ser. No. 943,082, Sep. 10, 1992, Pat. No. 5,335,655.

[51] Int. Cl.$^6$ .............................................. A61M 16/20
[52] U.S. Cl. .......................... 128/207.16; 128/207.14; 604/181
[58] Field of Search ............... 128/207.14, 207.16, 128/200.24; 604/181; 433/27, 95; 408/16; 15/339; 116/138; 137/607, 636.4, 888, 891

[56] References Cited

U.S. PATENT DOCUMENTS

| | | | |
|---|---|---|---|
| 975,645 | 11/1910 | Sherburne | 116/55 |
| 1,088,817 | 3/1914 | Graham | 116/55 |
| 2,376,971 | 5/1945 | Kleit . | |
| 2,638,096 | 5/1953 | Waldhans . | |
| 2,791,217 | 5/1957 | Iskander | 128/203 |
| 3,081,770 | 3/1963 | Hunter | 128/221 |
| 3,335,727 | 8/1967 | Spoto | 128/276 |
| 3,385,324 | 5/1968 | Wolf et al. | 137/636.4 |
| 3,818,539 | 6/1974 | Fortune | 15/339 X |
| 3,991,762 | 11/1976 | Radford | 128/276 |
| 4,011,828 | 3/1977 | Black | 116/70 |
| 4,291,691 | 9/1981 | Cabal et al. | 128/204.18 |
| 4,334,538 | 6/1982 | John | 433/95 |
| 4,346,702 | 8/1982 | Kubota | 128/207.14 |
| 4,569,344 | 2/1986 | Palmer | 128/207.14 |
| 4,648,868 | 3/1987 | Hardwick et al. | 604/32 |
| 4,792,327 | 12/1988 | Swartz | 604/22 |
| 4,818,227 | 4/1989 | Krueger | 433/27 |
| 4,856,564 | 8/1989 | Obal | 141/95 |
| 4,872,579 | 10/1989 | Palmer | 128/205.19 |
| 5,061,180 | 10/1991 | Wiele | 433/91 |
| 5,134,996 | 8/1992 | Bell | 128/207.14 |

FOREIGN PATENT DOCUMENTS

185442  8/1966  U.S.S.R. ........................ 128/207.14

*Primary Examiner*—Edgar S. Burr
*Assistant Examiner*—Eric P. Raciti
*Attorney, Agent, or Firm*—Andrew J. Beck; Montgomery W. Smith; Gene B. Kartchner

[57] ABSTRACT

A suction control valve is disclosed which includes a primary suction device access and an ancillary suction device access. The valve includes an actuator which is movable between a first position in which the primary access is closed against suction pressure therethrough, to a second position in which the primary access is open to suction pressure therethrough, or alternatively, to a third position in which the primary access port remains closed to suction pressure therethrough and the actuator becomes locked against movement into the second position. When the actuator is in the first position, atmospheric air can pass through the valve and into the suction pressure source in such a manner that a "hissing" auditory signal is generated, indicative of the presence of suction pressure within the valve. When the actuator is in the second or third positions, the "hissing" is prevented. The valve also includes an ancillary access port which allows the attachment of an ancillary suction device such as a Yankauer device to the valve without the necessity of removing the primary suction device from the primary device access port.

4 Claims, 7 Drawing Sheets

SUCTION CONTROL VALVE

This is a divisional of copending application(s) Ser. No. 07/943,082 filed on Sep. 10, 1992, now U.S. Pat. No. 5,335,655.

BACKGROUND OF THE INVENTION

1. Field of the Invention

This invention relates generally to fluid flow valving devices. More specifically, the present invention relates to a valving device for a suction catheter system. Even more specifically, the present invention relates to a suction control valve useable with suction catheters attachable to a respirator manifold of a respiratory system.

2. Prior Art

Respiratory systems used for the ventilation of critically ill patients are now commonly used in medical facilities. Typically, a prior art respiratory system includes a tracheal tube positioned either directly or through the nose or mouth into the trachea of a patient, a manifold connected to the tracheal tube at one port position thereof, a source of breathable gas connected at a second port thereof, and a third port for allowing exhausted gas to exit the manifold. The purpose of the respiration system is to assist the patient in maintaining adequate blood oxygenation levels without overtaxing the patient's heart and lungs.

While a patient is attached to a respiration system, it is periodically necessary to remove fluid from the patient's trachea or lungs. In the past, it was necessary to disconnect the respirator system, either by removing the manifold or by opening a port thereof, and inserting a small diameter suction catheter down the tracheal tube and into the patient's trachea and lungs. The fluid was then suctioned from the patient and the suction catheter was removed and the respirator system reassembled. Because of the necessary interruption in respiratory support caused by this procedure, a patient's blood oxygen often dropped to an unacceptably low level during the suctioning, even when other previously known breathing assisting efforts were simultaneously provided.

A known solution to the above problem has been to place a fourth port on the aspirator manifold which is adapted to receive a connector of a suctioning device. A suctioning device such as used with this type of aspirator manifold is adapted to allow a suction catheter to remain permanently positioned within the manifold without the necessity of attachment or removal thereof from the manifold in between uses, thereby avoiding substantial manifold pressure loss. The suction device includes an envelope which is sealed around the suction catheter in order to prevent contamination of the suction catheter surface which is repeatedly inserted into and removed from the patient's trachea and lungs. This type of suctioning device allows continuous respiratory support of the patient during suctioning of fluid from the patient's trachea and lungs, and is commonly controlled by means of a valve located in fluid flow connection between the catheter and the suction source therefore. A valve of this type which is generally exemplary of the prior art is shown in U.S. Pat. No. 4,872,579. The valve selectively communicates vacuum pressure into the interior of a catheter tube when it is desired to evacuate respiratory fluids. The valve is normally biased to a closed position to prevent vacuum flow until a user initiated manual displacement of a valve actuator opens the catheter tube to the vacuum source. The valve actuator is also designed to be rotatable relative to the remain of the valve between an open position and a closed position in which actuation for suctioning is prevented.

There nevertheless remain several draw backs associated with suction control valves of the prior art. For example, prior art suction control valves of the above described type fail to provide the user with an auditory indication of the continued availability of suction pressure for use. Further, when it becomes necessary to perform a suctioning procedure on the patient with other than the suction catheter to which the prior art valve is attached, as for example when a Yankauer device is required during a suctioning procedure in order to effect suctioning of the patient's mouth, it is necessary with the prior art suction control valves to disconnect the valve and suction catheter entirely from the suction source in order to replace them with the desired Yankauer device.

OBJECTS AND SUMMARY OF THE INVENTION

A principal object of the present invention is to provide a fluid flow valving device which is designed to provide the user with an auditory signal corresponding to the availability of pressure, including vacuum pressure, from a pressure source.

Another principal object of the present invention is to provide a fluid flow valving device designed with a locking and unlocking valve actuator which includes an auditory signaling means which informs the user of the locked or unlocked status of the valve.

It is further an object of the present invention to provide a fluid flow valving device which allows attachment of ancillary devices thereto for accessing the pressure or vacuum source without the necessity of removing a primary device therefrom.

Another object of the present invention is to provide a fluid flow valving device as part of a patient respiration system which can include a primary and/or ancillary device attached thereto such as a suction catheter and/or a Yankauer device, and allow access to the patient's mouth, trachea, or lungs, without interruption of continuous patient respiratory support.

A further object of the present invention is to provide a fluid flow valving device which is designed to allow attachment thereto of primary and ancillary devices such as a primary suction catheter attached to a patient respiration system which allows complete closure of the primary device and isolation thereof from the ancillary device such as a Yankauer suctioning device, whereby the fluid flow valving device functions as a connector only for the ancillary device to the source of pressure or suction and thus avoids any necessity of removing the fluid flow valving device from the source of pressure or suction in order to attach the ancillary device thereto.

These and other objects of the present invention are realized in a presently preferred embodiment thereof, described by way of example and not necessarily by way of limitation, which includes a fluid flow valving device for controlling suction through a preferred primary device, shown for purposes of description as a suction catheter device, and provides a connection port for an ancillary device such as a Yankauer suction wand.

The valve includes a main body forming a fluid flow channel therethrough and including an actuator for opening and closing the fluid flow passage of main body. The actuator is normally biased to a position in which the fluid flow passage is closed to prevent fluid passage therethrough and can be actuated by the user against the biasing thereof in order to open the fluid flow passage. The actuator may also be rotated relative to the valve body to a locking position in which the actuator can no longer be actuated. On each end of the fluid flow channel through the valve body, a tubular extension for attachment of the valve to a suction source and to a primary device is included.

The valve body also includes an ancillary device connection port positioned opposite the valve actuator which is normally closed with a flip top cap and can be opened to expose a connection port which is designed to receive an ancillary device such as a Yankauer suctioning wand therein. The port is in fluid flow connection with the fluid flow passage through the valve body which is in turn in fluid flow connection with the suction source to which the valve is attached.

DETAILED DESCRIPTION OF THE PREFERRED EMBODIMENT

As shown in the exemplary drawings for the purposes of illustration, an embodiment of a fluid flow valving device made in accordance with the principals of the present invention, referred to generally by the reference numeral 10, is provided for attachment to a suction source and a primary suctioning device and, when desired, to an ancillary suctioning device.

Figure 1:
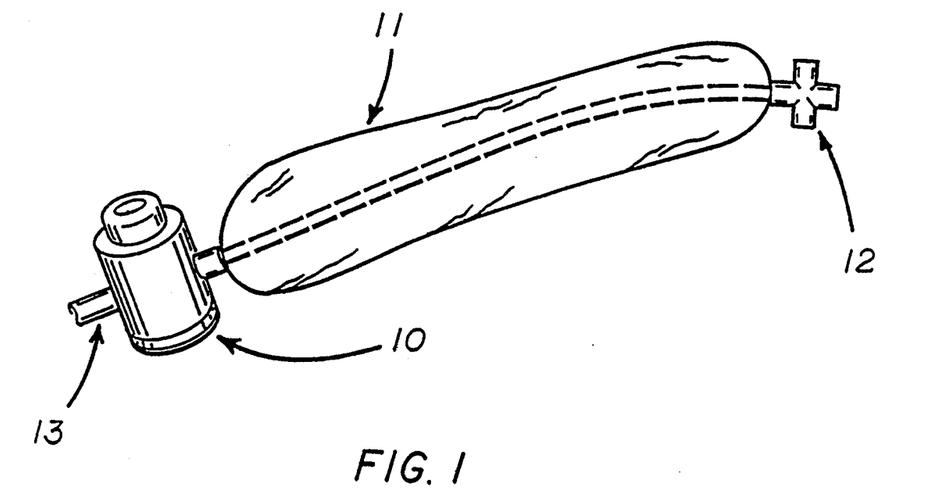
FIG. 1 shows a perspective view of a fluid flow valving device formed in accordance with the principals of the present invention attached to a suction source and a suction catheter designed for use with a respiratory support system.

More specifically, as shown in FIG. 1, the suction control valve 10 is shown attached to a suction catheter device 11 which is adapted to be used in conjunction with a patient respiratory support system through attachment to a respirator manifold such as the manifold 12. The valve 10 is also shown attached to a source of suction by means of a suction tube 13.

Figure 2:
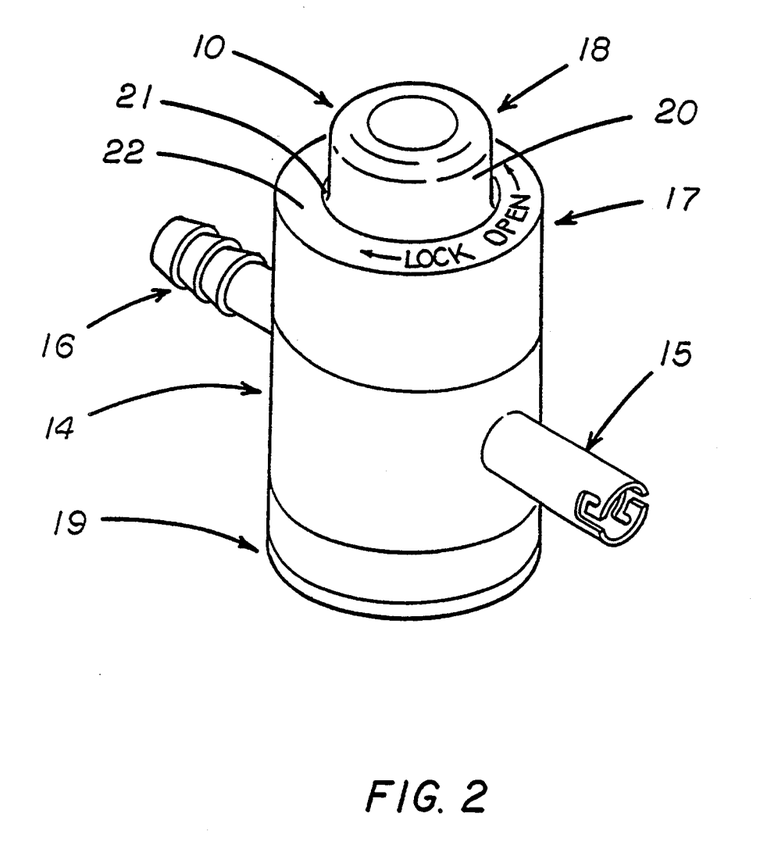
FIG. 2 is a perspective view of a fluid flow valving device formed in accordance with the principals of the present invention.

As shown in FIG. 2, the valve 10 of the present invention is formed of a generally cylindrical valve body 14 with a primary device connector 15 extending away therefrom in a radial direction and a suction source connector 16 extending away therefrom in a radial direction opposite the primary device connector 15. A lower cap 19 is formed to a cylindrical shape having the same diameter as the valve body 14 and covers the bottom of the valve body 14. An upper cap 17 is also formed into a generally cylindrical shape and is connected to the top of the valve body 14. A portion of the actuator 18, constituting the button 20, extends from the interior of the valve body 14 through the upper cap opening 21 and extends above the annular surface 22 of the upper cap 17. The positioning of the actuator 18 on the valve 10 is intended to allow for ease of manipulation thereof in a single hand of the user. The valve 10 is sized so as to be easily placeable within a user's palm such that the user's thumb may rest comfortably on the button 20 of the actuator, with the user's fingers curling about the lower cap 19 to support the valve 10 against the internal bias of the actuator 18 when the user presses on the button 20 to open a suction channel through the valve 10.

Figure 3:
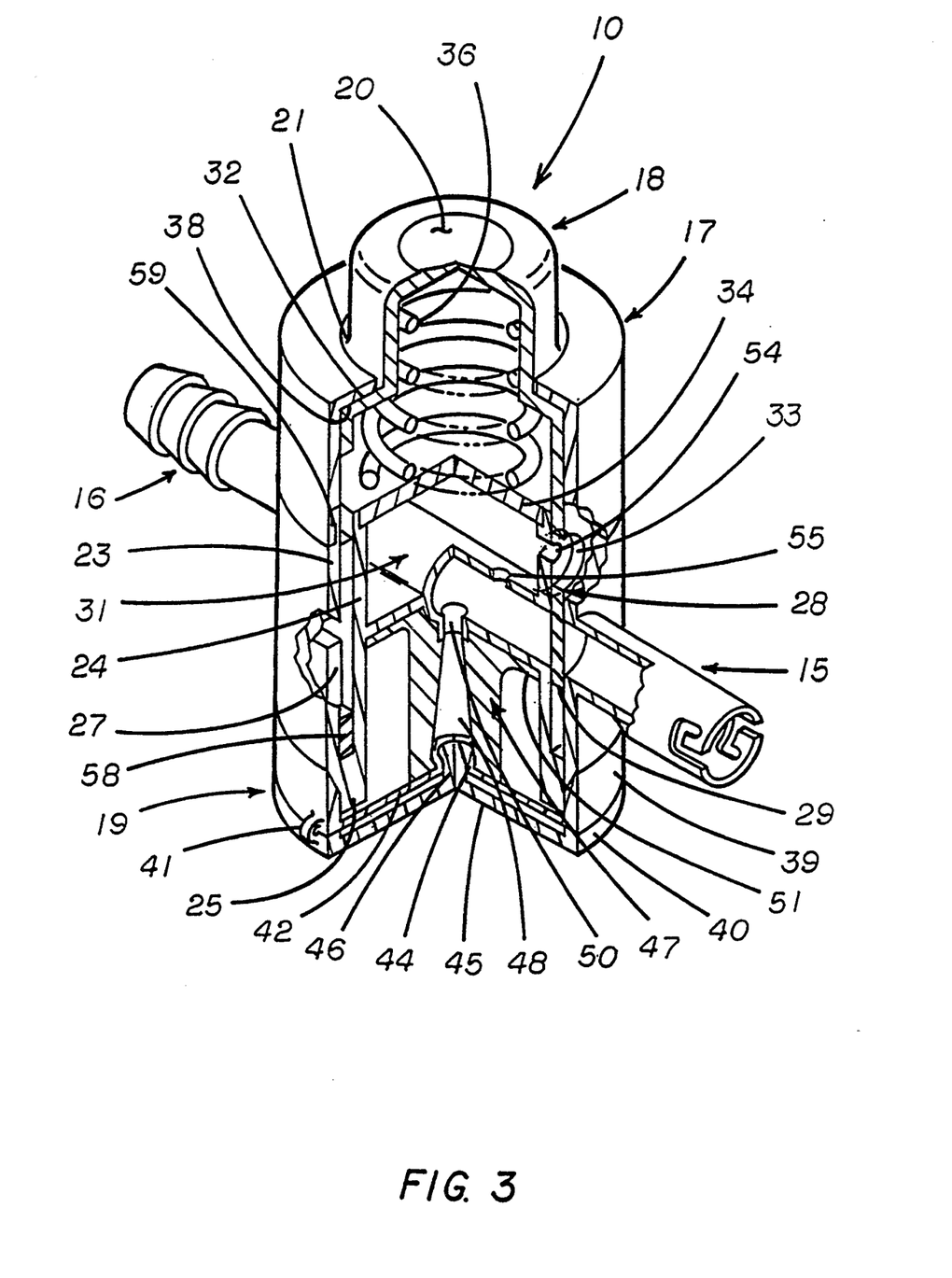
FIG. 3 is a cutaway view of the fluid flow valving device of FIG. 2.

Referring now to FIG. 3, the preferred internal structural arrangement of the valve 10 of the present invention will be explained, with the aid of FIGS. 4–6 which show various views of each individual component.

Figure 4:
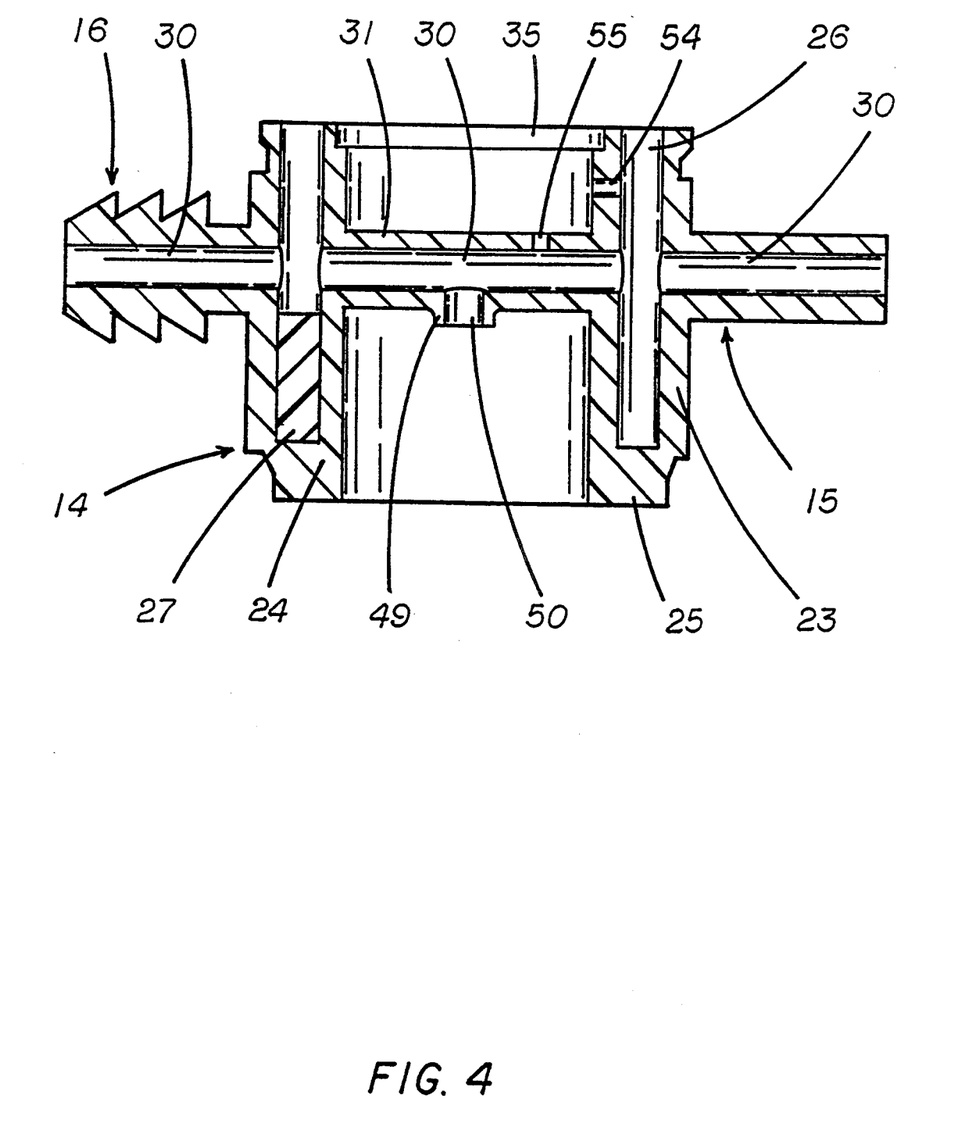
FIG. 4 is a cross-sectional view of the valve body of the fluid flow valving device of the present invention.

Referring specifically to FIGS. 3 and 4, the valve body 14 is formed generally of an exterior cylindrical member 23 and an interior cylindrical member 24 which are formed together at an annular base 25. The members 23 and 24 are formed in the shown orientation with an identical longitudinal axis, and are separated by the annular cylindrical passage 26. The passage 26 is formed to accept the semi-cylindrical actuator plate 28 (best shown in FIGS. 3 and 5) which is designed for translational and rotational movement there within for reasons which will be explained more fully below. A blocking member 27 is also located within the cylindrical passage 26 so as to be in a juxta opposed position relative to the actuator plate bottom surface 29 (see FIG. 5) when the actuator 18 is rotated to its locked position (see FIG. 9) in the manner and for the purpose as will also be explained below.

A fluid flow passage 30 is generally centrally formed within the valve body 14 so as to intersect with the longitudinal axis thereof in a perpendicular orientation. The fluid flow passage 30 is formed within the interior cylindrical member 24 by the rigid tubular member 31, and passes from the exterior cylindrical member 23 to pass through the primary device connector 15 and suction source connector 16. As can be seen in FIG. 4, the rigid tubular member 31 opens at both ends thereof directly into the annular cylindrical passage 26 at positions directly adjacent the primary device connector 15 and suction source connector 16. The entire fluid flow passage 30 is therefor essentially an elongate linear channel of uniform diameter passing through the cylindrical passage 26 at two diametrically opposed locations.

Figure 5:
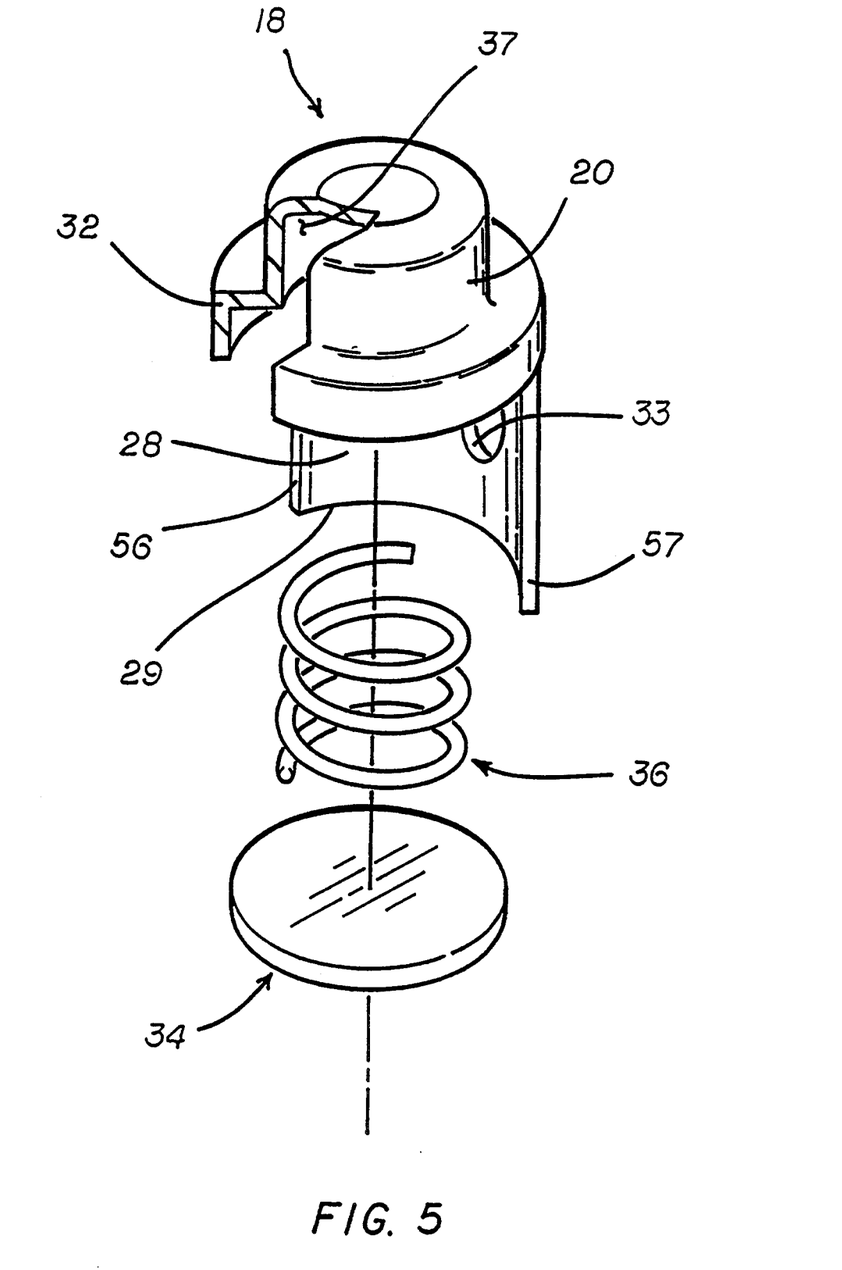
FIG. 5 is a partial cutaway view of the actuator of the fluid flow valving device of the present invention including the preferred embodiment of the biasing elements thereof.
Figure 6:
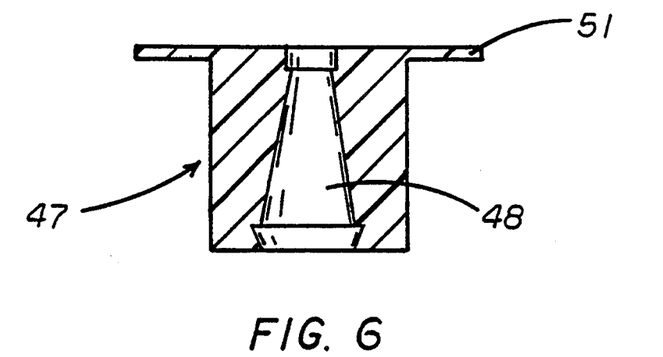
FIG. 6 is a cross-sectional view of an ancillary device connection port formed in accordance with the principals of the present invention.

As best shown in FIGS. 3 and 5, the actuator 18 includes the cylindrical button 20 which is surrounded by an annular shoulder 32. The semi-cylindrical actuator plate 28 extends from the annular shoulder 32 and forms a generally circular actuator opening 33 therein. The actuator 18 is positioned within the valve body 14 such that the actuator plate 28 is located within the annular cylindrical passage 26.

Figure 8:
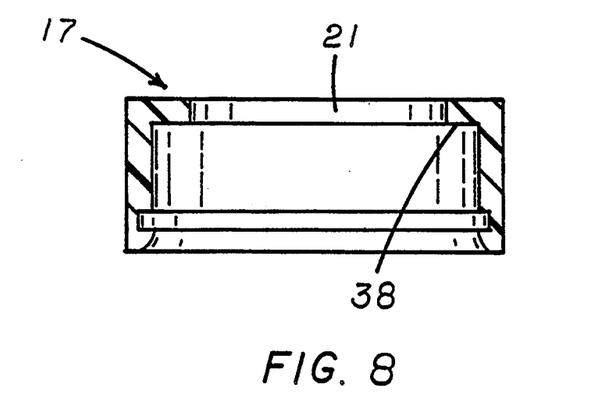
FIG. 8 is a cross-sectional view of an upper cap formed in accordance with the principals of the present invention used to retain the actuator in proper position within the valve body.

The supporting device 34 is positioned within the enlarged cylindrical channel 35 at the top of the interior cylindrical member 24 of the valve body 14 and the compression spring 36 is positioned between the supporting disks 34 and the interior 37 of the button 20 and operates to bias the actuator 18 upwardly. As best shown in FIGS. 3 and 8, the upper cap 17 includes a shoulder 38 which contacts the actuator annular shoulder 32 to hold it within the annular cylindrical passage 26. The upper cap 17 is attached to the valve body 15 preferably by means of a snap fit connection 59, but may be attached in any well known manner which is at least sufficiently strong to counteract the biasing force of the compression spring 36.

Figure 9:
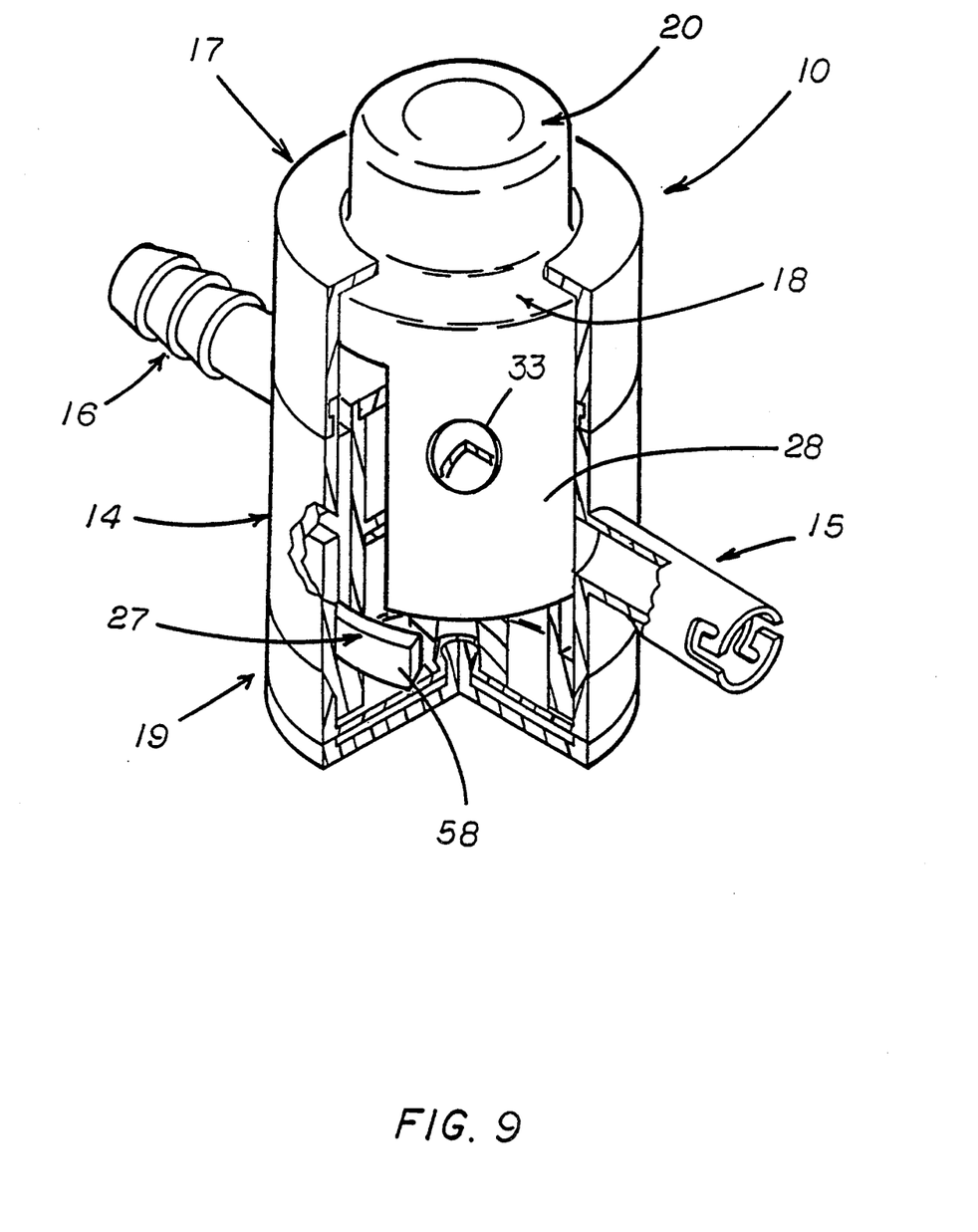
FIG. 9 is a cutaway view of the fluid flow valving body as shown in FIG. 3, modified to show the actuator rotated to the locked position.

As can be seen in FIG. 3, the actuator 18 can rotate within the cylindrical passage 26, and can translate along the longitudinal axis of the valve body 14 between a first position in which the annular shoulder 32 of the actuator 18 is in contact with the shoulder 38 of the upper cap 17, to a second position in which the actuator 18 is translated downwardly until the annular shoulder 32 thereof contacts the supporting disk 34. However, when the actuator 18 is rotated to the locked position such as is shown in FIG. 9, a portion of the actuator plate bottom surface 29 is located directly over an extension 58 of the blocking member 27 positioned in the bottom of the annular cylindrical passage 26. When rotated to the locked position, translational motion of the actuator 18 cannot occur. This aspect of the invention will be explained in more detail below in connection with the explanation of the operation of the valve 10.

Figure 7:
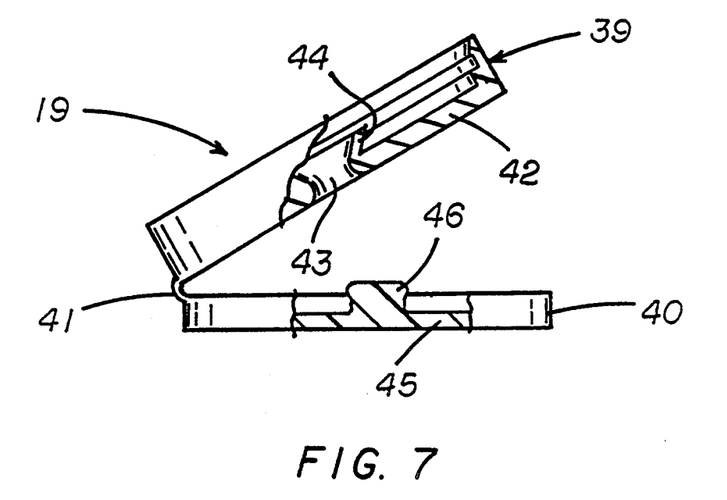
FIG. 7 is a partially cutaway view of a lower cap formed in accordance with the principals of the present invention used to cover and enclose the ancillary connection port within the valve body.

As shown in FIGS. 3 and 7, the bottom of the valve body 14 is covered with a lower cap or "flip cap" 19. The lower cap 19 is formed of a generally cylindrical shape having a diameter equal to the diameter of the valve body 14 and includes a fixed member 39 which is hingeably attached to a cover member 40 by means of hinge 41 which may be of the "living hinge" type and formed of polymeric material. The fixed member 39 is preferably attached to the annular base 25 of the valve body by an ultrasonic weld, however any well known attachment means may be used. The fixed member 39 includes a circular plate 42 which has an opening 43 formed centrally therein which is surrounded by an inwardly projecting boss 44. The cover member 40 of the lower cap 19 also includes a circular plate 45, on the interior surface of which a plug 46 is formed and sized so as to fit snugly within the fixed member opening 43 to form a fluid tight seal whenever the cover member 40 is closed over the fixed member 39.

Referring momentarily to FIG. 4, a boss 49 of the rigid tubular member 31 surrounds an opening 50 therethrough which passes into the fluid flow passage 30 of the rigid tubular member 31. As best shown in FIGS. 3 and 6, a bushing 47 is located within the valve body 14 between the rigid tubular member 31 and the circular plate 42. The bushing forms a fluid flow channel 48 therethrough which is shaped on each end thereof to connect with bosses 44 and 49 on the circular plate 42 and rigid tubular member 31 respectively in fluid tight relationship, thus allowing fluid flow connection of the bushing fluid flow channel 48 with the suction source through the fluid flow passage 30.

Figure 10:
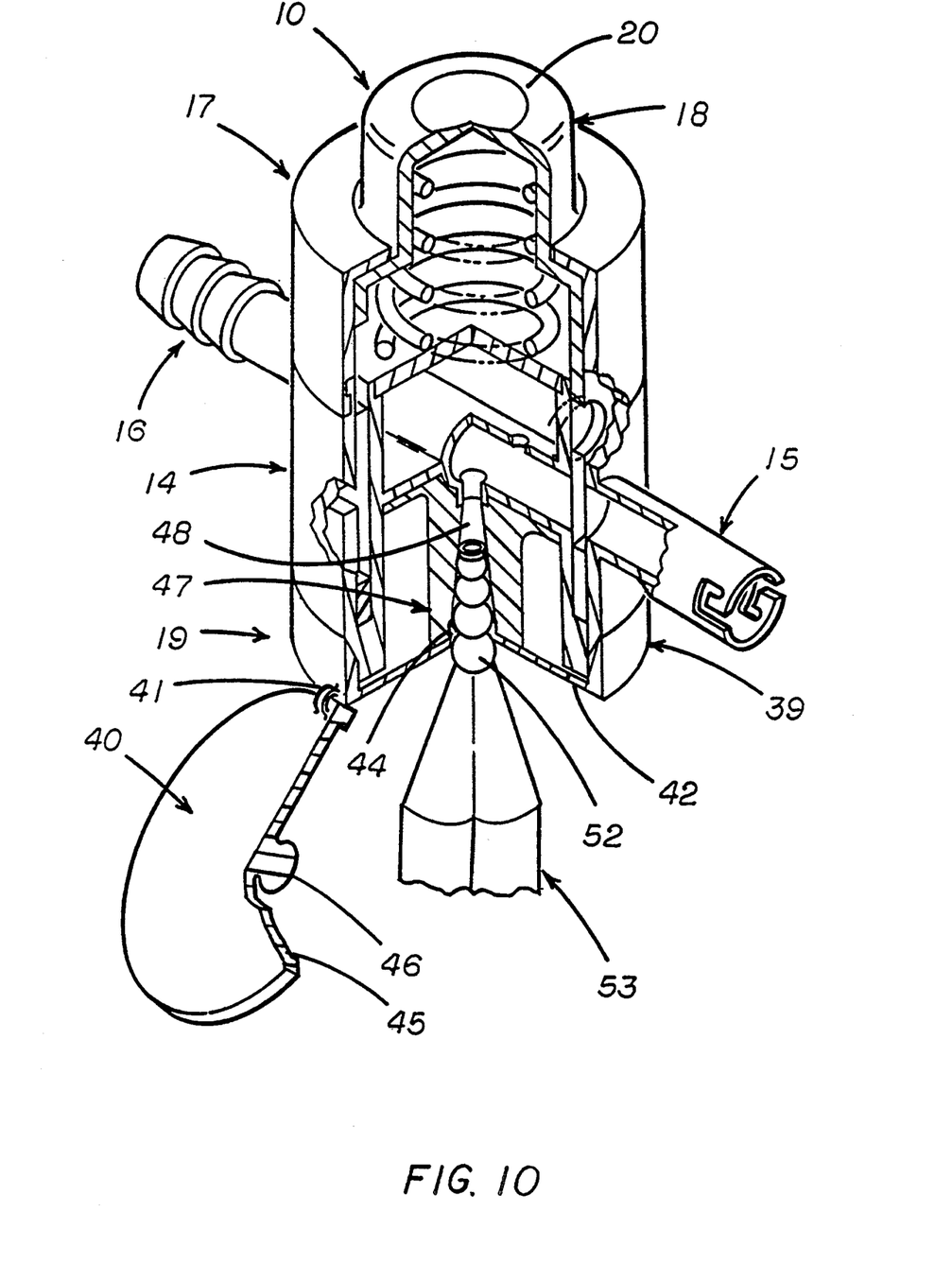
FIG. 10 is a partial cutaway view of the fluid flow valving body of the present invention shown attached to a Yankauer suctioning wand.

Referring again to FIGS. 3 and 6, the bushing 47 also includes an enlarged flange 51 at the top surface thereof which assists in surrounding the exterior surface of the rigid tubular member 31 to ensure a fluid tight seal between the boss 49 and the bushing 47. The bushing 47 is preferably formed of a soft polymeric material which can be deformed to accept and hold a relatively rigid connector of an ancillary device, such as the end connector 52 of a Yankauer suctioning wand 53 as shown in FIG. 10.

OPERATION OF THE PREFERRED EMBODIMENT

As shown in FIG. 1, preparation for operation of the valve 10 of the present invention includes attaching the primary device connector 15 thereof to the distal end of a primary device such as the suction catheter device 11, and attaching the suction source connector 16 to a suction tube 13 from a suction pressure source. When it is desired to administer suction to a patient, the suction catheter of the suction catheter device 11 is inserted into the patient's trachea or lungs, and the button 20 of the actuator 18 is rotated to the unlocked or opened position as best shown in FIG. 2 (referring to the annular surface 22 of the upper cap 17 on which arrows may be included showing the proper direction of rotation of the button 20 for unlocking the actuator 18).

When rotated to the unlocked position, the actuator 18 allows a bleed of suctioned atmospheric air to pass into the valve 10 through the upper cap opening 21. As best shown in FIG. 3, atmospheric air drawn into the upper cap opening 21 can move past the upper cap shoulder 38 and the actuator shoulder 32 into the annular cylindrical passage 26 of the valve body 14 where it is then drawn through the actuator opening 33 in the actuator plate 28 and the interior cylindrical member bleed opening 54 and the tubular member bleed opening 55 into the fluid flow passage 30 where it can be drawn out of the valve 10 into the suction pressure source. Movement of atmospheric air through the valve 10 into the suction source when the actuator 18 is in the open position generates an auditory signal, being a very recognizable "hissing" sound, which is indicative of the operation of the suction pressure source and the presence of suction pressure within the fluid flow passage 30. The interior cylindrical member bleed opening 54 is positioned on the interior cylindrical member 24 so that it will be oriented directly in line with the actuator opening 33 when the actuator 18 is rotated completely to its open position.

Although not completely shown in the drawings, the blocking member 27 is so positioned within the annular cylindrical passage 26 that rotation of the actuator 18 to the open position in which the actuator opening 33 thereof is aligned with the interior cylindrical member bleed opening 54 causes the side surface 56 (see FIG. 5) of the actuator plate 28 to abut against the blocking member 27. In this manner, when the user rotates the actuator 18 in the opened or unlocked direction until further rotation thereof is prevented by the blocking member 27, he or she is assured that the actuator opening 33 is properly aligned with the interior cylindrical member bleed opening 54.

When it is desired to initiate suctioning through the suction catheter device 11, the user forces the actuator button 20 downwardly into the valve body 14 against the bias of the compression spring 36. This linear translational movement of the actuator 18 relative to the valve body 14 causes the actuator plate 28 to move downwardly within the annular cylindrical passage 26. Since the actuator 18 has been previously rotated to its completely opened position, the actuator opening 33 in the actuator plate 28 is so positioned as to move into alignment with the fluid flow channel 30. As can be seen, the actuator plate 28 blocks the fluid flow channel 30 between the rigid tubular member 31 and the primary device connector 15 whenever the actuator 18 is in its fully upwardly extended or "released" position, but gradually moves out of blocking position as the actuator opening 33 is moved into alignment position with the fluid flow channel 30 as the actuator button 20 is depressed.

As can be seen, complete depression of the button 20 occurs when the actuator shoulder 32 contacts the supporting device 34. In the completely depressed position, the actuator opening 33 is completely aligned with the fluid flow channel 30 and presents no fluid flow obstacle therethrough. As is also readily evident, the amount of suction pressure allowed through the fluid flow channel 30 can be regulated from a "no flow" level when the button 20 is released, to gradually increasing flow levels as the actuator opening 33 is moved into alignment with the fluid flow channel 30 as the button 20 is depressed toward the support device 34.

It should be noted that when the actuator 18 is rotated to its complete open or unlocked position and then completely depressed until the actuator shoulder 32 abuts the support device 34 causing complete alignment of the actuator opening 33 with the fluid flow channel 30, fluid flow caused by the suction pressure source is allowed to pass directly through the valve 10 in a completely open and linear flow path, having no element of the valve 10 obstructing the passage of flow through the fluid flow channel 30. This is especially useful in the preferred intended use of the valve 10 of the present invention of suctioning fluids from a patient's mouth, trachea and lungs since it affords the clearest possible passageway through the valve 10 for fluids normally suctioned from the patient. Even clotted mucal material can pass easily through the valve 10 without the risk of clogging the fluid flow passage 30, since there are no obstructing valve elements anywhere therethrough.

As is evident, movement of the actuator plate 28 downwardly caused by depression of the button 20 causes the actuator opening 33 to move downwardly past the interior cylindrical member bleed opening 54 and the actuator plate 28 to block the flow of atmospheric air therethrough. Thus, whenever the actuator button 20 is depressed, bleeding of atmospheric air into the fluid flow channel 30 through the openings 54 and 55 is prevented. This causes the "hissing" of the valve 10 to stop, thus providing the user with another audio indication of the proper operation of the valve 10. The user immediately recognizes the arresting of the "hissing" sound upon depression of the actuator button 20, which signals the user that the suction pressure has been diverted into the suction catheter device 11. In this way, the presence or absence of the "hissing" sound provided by the valve 10 of the present invention to the user assists in the user in confirming proper operation of the valve 10.

When the actuator button 20 is released after suctioning through the suction catheter device 11 is completed, the actuator opening 33 moves upwardly, due to the bias of the compression spring 36, to again align with the interior cylindrical member bleed opening 54. The valve then again begins to generate the "hissing" auditory signal. Upward movement of the actuator 18 is arrested by the abutment of the actuator shoulder 32 against the upper cap shoulder 38 of the upper cap 17.

At times it is convenient, and even important from a safety consideration for a patient, to ensure that the actuator button 20 cannot be depressed to allow suction pressure through the suction catheter device 11. If it is desired to prevent suctioning through the suction catheter device 11, the user may rotate the actuator 18 (by rotating actuator button 20 in the direction shown on the upper cap surface 22 in the direction of the locking arrow) to lock the actuator 18 against depression.

As best shown in FIG. 9, rotation of the actuator 18 causes the actuator plate 28 to rotate within the annular cylindrical passage 26. Rotation is allowed to continue until the side surface 57 of the actuator plate 28 abuts against the blocking member 27. In this position, the actuator plate bottom surface 29 is positioned directly above a blocking member extension 58. Any attempt to depress the actuator button 20 when in the locked position will fail to allow fluid flow through the fluid flow passage 30 since linear downward translational movement of the actuator 18 is prevented by the extension 58 of the blocking member 27, and the actuator plate 28 completely blocks the fluid flow passage 30 between the rigid tubular member 31 and the primary device connector 15.

Further, whenever the actuator 18 has been rotated to the locking position, the actuator opening 33 is rotated out of alignment with the interior cylindrical member bleed opening 54. Therefore, bleed of atmospheric air into the fluid flow passage 30 is prevented and the user is aware of such by the absence of the "hissing" auditory signal.

This feature of the present invention allows a user to lock the actuator 18 against accidental actuation by a patient such as may accidentally occur if the valve 10 and suction catheter device 11 are left attached to a respiration manifold 12 providing respiratory support to a patient. Although a patient may inadvertently attempt to depress the actuator 18, for example by accidentally rolling over on top of the valve 10, the suctioning of fluid through the suction catheter device 11 will not occur when the actuator 18 is in the locked position. Further, the medical personnel or other users of the valve 10 will be provided an auditory signal (absence of hissing) whenever the valve 10 is locked against actuation, and a different auditory signal (the presence of hissing) whenever the valve 10 is unlocked or opened. This can be extremely convenient and add an additional safety factor to the use of the valve 10 in that it is not necessary for the user to see directly whether or not the valve 10 is locked against actuation, because an auditory hissing signal is generated whenever the valve 10 is open, which signals the user that the valve 10 must be attended to or locked in order to avoid possible injury to the patient.

The valve 10 of the present invention may also operate as a connector for an ancillary suctioning device such as a Yankauer 53 if desired. As shown in FIG. 10, when it is desired to attach an ancillary device to the valve 10 of the present invention, the user merely rotates the cover member 40 of the lower cap 19 to an open position. The end connector 52 of a Yankauer suction wand 53 or other ancillary device may then be inserted through the fixed member circular plate opening 43 and into the bushing fluid flow channel 48 which is designed to generate a friction fit therewith to hold the Yankauer 53 in connection with the valve 10. As can be seen, attachment of a Yankauer 53 in this manner provides immediate connection thereof with the suction pressure source attached to the valve 10 through the bushing fluid flow channel 48 and the valve body fluid flow passage 30.

Attachment of an ancillary device to the valve 10 without requiring detachment of the primary device 11 therefrom can be very important in many procedures involving suctioning of fluids from a patient attached to a respiratory support system. Since serious detriment to the patient can occur whenever it is necessary to breach the integrity of the respiratory support system, the avoidance of disassembly of any equipment, or detachment of the suction source, becomes a positive procedural improvement.

As can be seen with the present invention, the ability to attach a Yankauer 53 to the valve 10 to allow suctioning of the patient's oral cavity without the necessity of disassembling any part of the system in place for primary suctioning of the patient's trachea and lungs is an important improvement over the prior art.

When the Yankauer 53 is no longer needed, it can be detached from the valve 10 and the cover member 40 can again be closed to block the bushing fluid flow channel 48 and seal it against fluid flow therethrough. It should be noted that suctioning through the ancillary port connection of the valve 10 can be accomplished regardless of the positioning of the actuator 18. However, it is preferable that the actuator 18 be rotated to the locked position prior to use of the ancillary device port in order to prevent bleed-by of atmospheric air into the fluid flow passage 30 which would tend to weaken the suction pressure through the Yankauer 53.

It will be apparent from the foregoing that, while a particular embodiment of the present invention has been illustrated and described, various modifications can be made thereto without departing from the spirit and scope of the invention. Accordingly, it is not intended that the invention be limited, except as by the appended claims.

I claim:

1. A suction control valve comprising:
    a valve body having a suction source connector, a primary suction device connector, an ancillary suction device access port, and a fluid flow passage for allowing fluid flow between said suction source connector and said primary suction device connector and said ancillary suction device access port, and
    an actuator positioned at least partially within said valve body for opening and closing said primary suction device connector from fluid flow therethrough and having at a first position in which said primary suction device connector is closed against fluid communication with said suction source connector, a second position in which said primary suction device connector is open to fluid communication with said suction source connector; and a plurality of third positions wherein said primary suction device connector is in varying degrees of fluid communication with said suction source connector; wherein said ancillary suction device access port includes a cap having a cover member hingeably movable between a closed position and an open position.

2. A suction control valve according to claim 1 wherein said ancillary suction device access port includes a cap independent of said actuator for opening and closing said ancillary suction device access port from fluid flow therethrough.

3. A suction control valve according to claim 1 wherein said ancillary suction device access port includes a relatively flexible bushing having a bushing fluid flow channel therethrough which is in fluid flow connection with said fluid flow passage, said bushing being held within said valve body by said cap.

4. A suction control valve according to claim 3 wherein said cover member in said closed position inhibits fluid flow through said bushing fluid flow channel, and in said open position allows insertion of an ancillary suction device into said bushing fluid flow channel.

* * * * *